(12) United States Patent
Zheng

(10) Patent No.: US 10,524,895 B2
(45) Date of Patent: Jan. 7, 2020

(54) COLLAGEN CONSTRUCT AND METHOD FOR PRODUCING THE COLLAGEN CONSTRUCT

(71) Applicant: Orthocell Limited, Murdoch (AU)

(72) Inventor: Ming Hao Zheng, City Beach (AU)

(73) Assignee: Orthocell Limited, Murdoch, W.A. (AU)

( * ) Notice: Subject to any disclaimer, the term of this patent is extended or adjusted under 35 U.S.C. 154(b) by 89 days.

(21) Appl. No.: 15/514,804

(22) PCT Filed: Oct. 12, 2015

(86) PCT No.: PCT/AU2015/000611
§ 371 (c)(1),
(2) Date: Mar. 27, 2017

(87) PCT Pub. No.: WO2016/054686
PCT Pub. Date: Apr. 14, 2016

(65) Prior Publication Data
US 2017/0216014 A1     Aug. 3, 2017

(30) Foreign Application Priority Data

Oct. 10, 2014 (AU) ................................ 2014904065

(51) Int. Cl.
*A61F 2/08*      (2006.01)
*A61L 27/24*     (2006.01)
*A61F 2/00*      (2006.01)

(52) U.S. Cl.
CPC .............. *A61F 2/08* (2013.01); *A61L 27/24* (2013.01); *A61F 2/0095* (2013.01); *A61F 2240/001* (2013.01); *A61L 2430/10* (2013.01)

(58) Field of Classification Search
CPC .......... A61F 2/08; A61L 27/24; A61L 2430/10
See application file for complete search history.

(56) References Cited

U.S. PATENT DOCUMENTS

| 4,772,288 A | 9/1988 | Borner et al. |
| 5,755,791 A * | 5/1998 | Whitson ................. A61F 2/02 424/424 |

(Continued)

FOREIGN PATENT DOCUMENTS

| EP | 2098253 | 9/2009 |
| WO | 0072782 | 12/2000 |

(Continued)

*Primary Examiner* — William H Matthews
(74) *Attorney, Agent, or Firm* — Carol L. Francis; Bozicevic Field & Francis LLP

(57) ABSTRACT

There is disclosed a collagen construct comprising a plurality of elongate strips, wherein each strip contains a plurality of collagen fibres that are substantially aligned along the length of the respective strips, and the strips are braided or woven together to produce a collagen construct in the form of a rope that can be used for replacing tendons or ligaments, such as cruciate ligaments. Also disclosed is a method for making or producing the collagen construct from a collagen membrane having a plurality of collagen fibres being substantially aligned parallel to each other in a common direction. The membrane is cut along cut lines that are orientated substantially parallel to that common direction, thereby to separate elongate strips from the membrane. The strips are then braided or woven together to form the collagen construct.

13 Claims, 2 Drawing Sheets

(56) References Cited

U.S. PATENT DOCUMENTS

| | | | |
|---|---|---|---|
| 8,492,332 B2 * | 7/2013 | Paukshto | A61L 27/24 514/7.2 |
| 9,096,688 B2 | 8/2015 | Zheng | |
| 9,644,177 B2 * | 5/2017 | Kim | C12N 5/0068 |
| 10,314,939 B2 | 6/2019 | Zheng | |
| 2004/0024457 A1 * | 2/2004 | Boyce | A61F 2/08 623/13.17 |
| 2008/0200992 A1 | 8/2008 | Koob et al. | |
| 2009/0287308 A1 | 11/2009 | Davis et al. | |
| 2010/0298937 A1 * | 11/2010 | Laurencin | A61F 2/08 623/13.14 |
| 2012/0093877 A1 | 4/2012 | Zheng | |
| 2012/0276150 A1 | 11/2012 | Lauritzen et al. | |
| 2012/0301507 A1 | 11/2012 | Zheng | |
| 2013/0158342 A1 | 6/2013 | Chan et al. | |
| 2013/0323199 A1 | 12/2013 | Saku et al. | |
| 2014/0147494 A1 | 5/2014 | Cheng | |
| 2014/0288271 A1 | 9/2014 | Zheng | |
| 2017/0224344 A1 | 8/2017 | Zheng | |

FOREIGN PATENT DOCUMENTS

| | | |
|---|---|---|
| WO | 2000072782 | 12/2000 |
| WO | 0134065 | 5/2001 |
| WO | 2013185173 | 12/2013 |
| WO | 2006026554 | 3/2016 |

* cited by examiner

COLLAGEN CONSTRUCT AND METHOD FOR PRODUCING THE COLLAGEN CONSTRUCT

FIELD

The present invention relates to a collagen construct and to a method for producing the collagen construct.

More particularly, the present invention relates to a collagen construct in the form of a string or rope for use in replacing tendons and ligaments, such as anterior cruciate ligaments (ACL) which have ruptured.

BACKGROUND

Ligaments are specialized connective soft tissues which connect different organs or tissues and attach bone to bone. In the latter case, ligaments provide stability to joints by being flexible enough to allow natural movement of the bones yet also are strong and inextensible to prevent resistance to applied forces. Tendons connect muscle to bone and are capable of withstanding tension. In addition, tendons passively modulate forces during locomotion, providing additional stability with no active work. Their elastic properties allow tendons to store and recover energy at high efficiency. In tendons and ligaments, bundles of collagen fibres are embedded in a connecting matrix made of proteoglycans components. These bundles of collagen fibres provide the load carrying elements. In tendons, the collagen fibres are arranged in nearly parallel formation, thus enabling them to withstand high unidirectional loads. In ligaments, the collagen fibres are arranged in a less parallel formation, thereby enabling them to withstand predominant tensile stresses in one direction and smaller stresses in other directions.

Every year, hundreds of thousands of people sprain, tear, or rupture ligaments in particular in the knee, shoulder, and ankle or suffer from injuries to tendons of the upper and lower extremities, in particular in the shoulder, knee, foot, and ankle. One such ligament often affected by these types of injuries is the anterior cruciate ligament (ACL) of the knee. The ACL serves as a primary stabilizer of anterior tibial translation and as a secondary stabilizer of valgus-varus knee angulation, and is often susceptible to rupture or tear resulting from a flexion-rotation-valgus force associated with sports injuries and traffic accidents. Ruptures or tears often result in: severe limitations in mobility; pain and discomfort; and an inability to participate in sports and exercise. More than 200,000 people in the U.S. alone tear or rapture their ACL each year, leading to costs of approximately $3 billion for ACL reconstructive surgery and extensive rehabilitation. It is widely known that the ACL has poor healing capabilities. Total surgical replacement and reconstruction are required when the ACL suffers a significant tear or rupture resulting in joint instability. The most common practice is to reconstruct a torn ACL by substituting the torn ligament with the patient's own tissue, also known as an autograft. Other options for substitute ligaments include donor tissues from another organism, also known as allografts, as well as synthetic grafts.

Surgeons have considered ligament constructs comprising collagen fibres, biodegradable polymers and composites thereof. When it comes to synthetic grafts the graft material is sometimes composed of linear arrangements of natural collagen fibres; however, this arrangement often makes repairing ruptured or lacerated tendons difficult. Also depending upon the nature of the repair, the tensile strength is not optimal. Accordingly, there is a continued need for replacement material, especially for ACLs, which has both the appropriate mechanical strength and also the appropriate physical properties to enable surgical implantation.

It is to be understood that, if any prior art publication is referred to herein, such reference does not constitute an admission that the publication forms a part of the common general knowledge in the art in any country.

SUMMARY

According to one aspect, there is provided a collagen construct comprising:
   a plurality of elongate strips, each strip having a length;
   each strip comprising a plurality of collagen fibres that are substantially aligned along the length of the respective strips;
   wherein the strips are amassed together to produce the collagen construct.

At least one of the collagen fibres in each strip may extend continuously along the entire length of its respective strip.

At least 50%, alternatively at least 80%, of the collagen fibres in each strip may extend continuously along the entire length of each respective strip.

In one embodiment each strip may have a thickness of 50 µm to 400 µm. In another embodiment each strip may have a thickness of 100 µm to 200 µm.

In one embodiment each strip may have a width of 50 µm to 5 mm. In another embodiment each strip has a width of 1 mm to 3 mm.

The plurality of the strips may be braided, plaited, woven or twisted together to form one or more collagen ropes.

A plurality of the collagen ropes may be braided, plaited, woven or twisted together to form one or more collagen cables.

The collagen construct may have a length of 0.5 cm to 50 cm. In one embodiment the collagen construct may have a length of 2 cm to 20 cm.

The collagen construct may have a cross sectional area of 0.002 mm$^2$ to 18 mm$^2$. In one embodiment the collagen construct may have a cross sectional area of 0.6 mm$^2$ to 2 mm$^2$.

The collagen construct may be able to withstand a tensile load of 650 N without breaking or suffering any permanent deformation or damage.

The collagen construct may comprise a tendon or ligament prosthesis. In one embodiment the prosthesis may be an anterior cruciate ligament prosthesis.

According to another aspect, there is provided a method for producing a collagen construct comprising the steps of:
   a) forming a collagen membrane comprising numerous collagen fibres, wherein a majority of the fibres are substantially aligned parallel to each other in a common direction;
   b) cutting the membrane along cut lines that are orientated substantially parallel to the common direction, thereby to separate elongate strips from the membrane; and
   c) amassing together the elongate strips to form the collagen construct.

The method may comprise the step of treating the membrane with acetone and subsequently drying the membrane, thereby to fix the collagen fibres in their aligned orientation.

The method may comprise cutting the membrane in a manner so that each strip has a width sufficient that at least one of the collagen fibres extends continuously along the entire length of its respective strip.

The step of amassing the strips may comprise braiding, plaiting, weaving, twisting or winding together a plurality of the collagen strips to produce a collagen rope.

The method may comprise amassing sufficient strips so that the collagen rope has a cross sectional area of 0.002 mm² to 18 mm².

The method may comprise amassing sufficient strips together to produce a collagen rope of a sufficient size for use as an anterior cruciate ligament prosthesis.

The invention extends to providing a medical kit for anterior cruciate ligament replacement comprising a collagen construct described herein that is enclosed in a sterile package.

The invention further extends to a collagen construct as described herein, and to a collagen construct produced by a method as described herein, for use in replacing a tendon or ligament, such as an anterior cruciate ligament.

According to another aspect there is provided a method of repairing anterior cruciate ligament tears, partial or complete, comprising:

providing a collagen construct as described herein;
implanting the collagen construct to augment, repair or replace the anterior cruciate ligament; and
securing the collagen construct in place.

Yet other embodiments of the present disclosure are directed to an implantable collagen construct in the form of a rope that provides a new and alternative replacement for a ligament or tendon, such as an anterior cruciate ligament (ACL) that has ruptured.

In some embodiments, the implantable collagen construct is constructed out of a plurality of collagen fibres that are braided and/or woven together so that it is able to withstand a maximum tensile load of 650 N without breaking or suffering any permanent deformation or damage. In one embodiment the collagen construct has a diameter of ≤10 mm and a cross-sectional area of about 75-80 mm².

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE FIGURES

The present invention will now be described, by way of example, with reference to the accompanying schematic drawings, in which.

DETAILED DESCRIPTION OF SPECIFIC EMBODIMENTS

Figure 1:
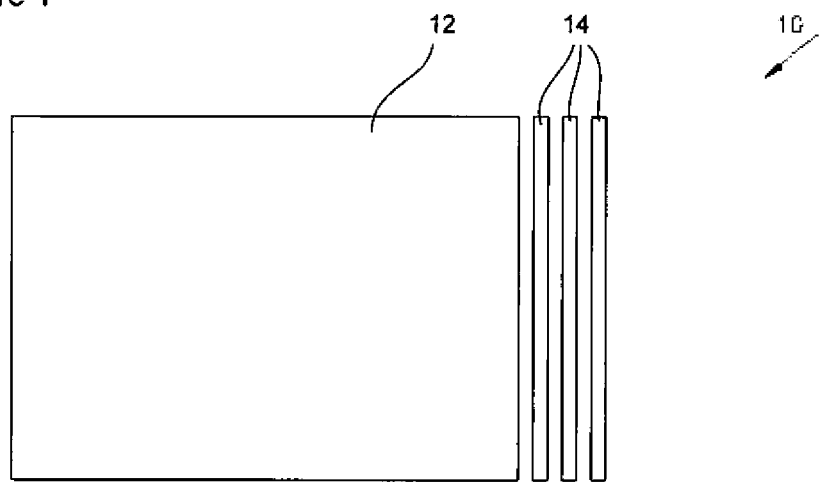
FIG. 1 shows a collagen scaffold arranged to be cut into elongated strips.

The present invention now is described more fully hereinafter with reference to the accompanying figures, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y". As used herein, phrases such as "from about X to Y" mean "from about X to about Y".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" and "construct" are used interchangeably herein to designate an implantable collagen construct in the form of a collagen rope or string configured to replace (at least a portion of) a natural tendon or natural ligament of a mammalian subject (for veterinary or medical (human) applications). The ligament can be the anterior cruciate ligament. The term "implantable" means the collagen construct can be inserted, embedded, grafted or otherwise chronically attached or placed on or in a patient.

The term "collagen construct" as used herein, refers to a material that comprises collagen. The collagen construct can be in a finished or final form for use or in an unfinished or pre-final form. The collagen construct can comprise natural collagen, natural collagenous tissue, synthetic collagen, and/or any combination thereof. The term "synthetic collagen" as used herein, refers to collagen material that has been formed and chemically and/or physically altered from its naturally occurring state into an elongate fibre or bundle of collagen fibres. In one embodiment the collagen material can be obtained from a collagen membrane produced according to a method as described in WO 2013/185173. In other embodiments the collagen can be non-denatured collagen, such as whole or fragmented native collagen fibres from tendon or skin.

Exemplary collagen constructs include, but are not limited to, collagen fibres and collagen fibre bundles that are arranged into cords, twisted cords, strips, braids, plaits, weaves, cables, ligament or tendon prosthesis, and the like. The collagen fibres or fibre bundles can be spun, twisted, woven, plaited or braided to define a respective spun, twisted, woven, plaited or braided collagen construct.

Collagen fibres are composed of three polypeptide chains that intertwine to form a right-handed triple helix. Each collagen polypeptide chain is designated as an α chain and is rich in glycine, proline and hydroxyproline. There are a number of different α chains and different combinations of these α chains correspond with different types of collagen. In some embodiments, the collagen membrane of the present invention comprises type I collagen. Type I collagen is composed of two α1 chains and one α2 chain.

In some embodiments, the collagen fibres or bundles are provided from dense connective tissue isolated from a source. The term "dense connective tissue" as used herein refers to the matrix comprised primarily of type I collagen fibres or bundles found in the tendons, ligaments and dermis of all mammals. Dense connective tissue is distinct from "loose connective tissue". Loose connective tissue is characterised by loosely arranged fibres and an abundance of cells and is present, for example, beneath the epithelia that covers body surfaces and lines internal organs.

In some embodiments, the present invention provides a collagen membrane comprising greater than 80% type I collagen. In other embodiments, the collagen membrane comprises at least 85% type I collagen. In still other embodiments the collagen membrane comprises greater than 90% type I collagen.

Collagen "microfibrils," "fibrils," "fibres," and "natural fibres" refer to naturally-occurring structures found in a ligament. Microfibrils are about 3.5 to 50 nm in diameter. Fibrils are about 50 nm to 50 μm in diameter. Natural fibres are above 50 μm in diameter. In some embodiments, the fibres and/or collagen construct can contain cells, engineered cells, stem cells, and the like, as well as combinations of the above.

The term "suture" refers to a flexible elongate material that is used to attach the collagen construct to a target anatomical structure to help hold the collagen construct in location in a body. The suture may be resorbable or non-resorbable, synthetic or natural. The suture can be configured to hold the implant in location for at least an initial post-implantation period of at least about 1 week, but may reside permanently in the body or, as noted above, may be substantially resorbable over time. The suture can be a single filament or multi-filament (braided) thread, floss, gut or wire, or combinations thereof that can be used to hold a portion of an implant against or attached to target structures, typically to bone and/or tissue. The suture may comprise a resorbable or non-resorbable biocompatible material. Examples of suture materials include elastomeric materials, such as polymers, copolymers and/or derivatives thereof, including Vicryl™, as well as other materials including NITINOL, and combinations thereof. The suture may be used to with a suture anchor (bone or tissue anchor).

The term "flexible" means that the so-called member can be flexed or bent.

The terms "braided" and "woven" and derivatives thereof mean to braid and/or (inter)weave, interlace and/or interlock in any manner, a plurality, typically three or more, fibres or bundles of fibres together, including manually or automatically weaving, braiding, knitting and/or knotting and combinations of these or other interlocking or interlaced constructions.

Referring to FIG. 1 there is shown a collagen scaffold 10 comprising a collagen membrane 12. The membrane 12 is in the form of a substantially flat web or sheet from which respective elongate strips 14 can be repeatedly cut, either until the entire membrane 12 is cut into such strips 14 or until sufficient strips 14 are obtained. Such cutting will normally be done using a laser cutter, but could also be done using conventional mechanical cutters or scissors.

Although the membrane 12 is shown to be rectangular in shape when seen in plan view, it will be appreciated that the membrane 12 can be provided in any other geometrical shapes, for example such as circular, oval, or trapezoidal. The particular shape of the membrane 12 may be dependent on the source from which the membrane 12 is obtained. The term "source" as used herein refers to any collagen tissue containing dense connective tissue in any mammal. In some embodiments, the tissue containing dense connective tissue is a tendon. A tendon is the tissue which connects muscle to bone in a mammal. In some embodiments, the collagen-containing tissue may be isolated from any mammalian animal including, but not limited to a sheep, a cow, a pig or a human. In other embodiments, the collagen-containing tissue is isolated from a human.

In the exemplary embodiment, the membrane 12 is produced according to a method as described in WO 2013/185173.

The membrane 12 comprises a collagen containing tissue segment obtained from a porcine inner organ lining that was treated to remove all non-collagenous tissue from the segment. In an initial treatment all the fatty tissue was physically removed from the tissue segment, whereafter the tissue segment was subjected to chemical treatment to denature non-collagenous proteins. Subsequently the tissue segment was centrifuged and washed to remove residual solutions and nucleic acids from the tissue segment. The tissue segment was stretched on a frame to reduce its cross-sectional thickness, to yield the membrane 12 having a desired thickness. The thickness of the membrane 12 is selected dependent on the intended use of the collagen construct, e.g. the requisite diameter of a collagen construct to be formed from the membrane 12, such as can be used for replacing an anterior cruciate ligament (ACL) which has ruptured. In one embodiment the membrane 12 has a thickness of between 50 μm to 400 μm. In another embodiment the membrane 12 has a thickness of between 100 μm to 200 μm. In yet a further embodiment the membrane 12 has a thickness of about 100 μm.

The membrane 12 can be treated with acetone and air-dried while still stretched on the frame so that the collagen fibres and fibre bundles therein become fixed in their natural alignment. However, it will be appreciated that other methods for fixing the collagen fibres in their natural alignment are also possible, such as alkaline-acid treating the membrane 12. Thereafter the membrane 12 can be compressed and/or rolled to create a smooth surface on opposed faces of the membrane 12.

Figure 2:
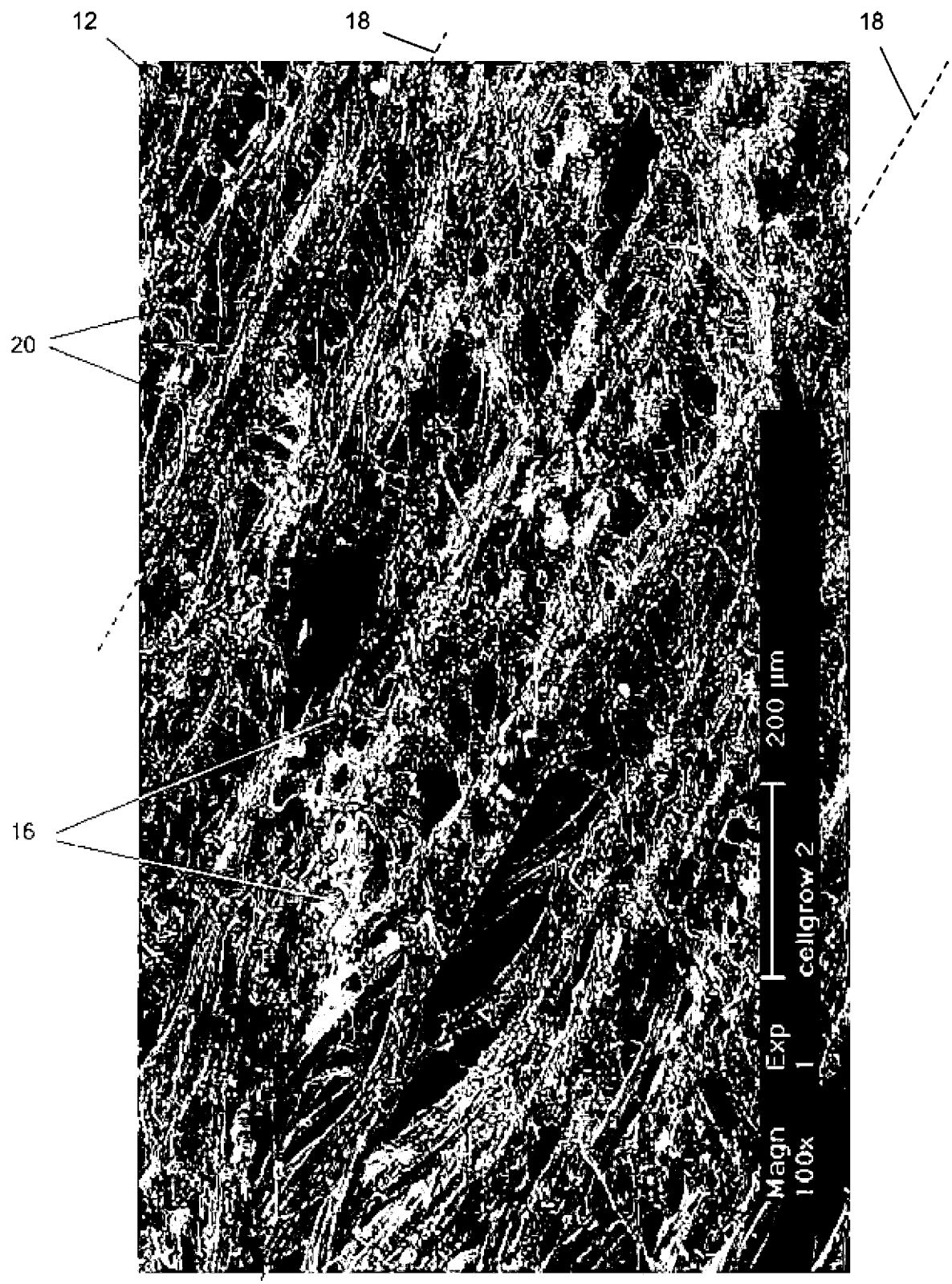
FIG. 2 shows a scanning electron microscopy (SEM) image of the collagen scaffold of FIG. 1 at ×100 magnification.

FIG. 2 shows a scanning electron microscopy (SEM) image (×100) of the membrane 12. It can be seen that the membrane 12 comprises numerous fibres 16, a majority of which are substantially aligned with each other in a common direction. Many of the fibres 16 may be substantially parallel to each other. As can be seen, the alignment of the fibres 16 results in the membrane 12 having a clear microscopic grain, similar to what would be found in a sheet of paper. The fibres 16 can branch into smaller fibres or fibrils, which can recombine with each other or with other fibres 16. Thus the fibres 16 form an interlinked web in the membrane 12. A number of microfibrils and/or fibrils 20 project transversely from the fibres 16, which assist in interlinking the web of the membrane 12.

When cutting the strips 14 from the membrane 12, the direction or orientation of a cut line 18 along which the membrane 12 is to be cut is aligned with the microscopic grain, i.e. aligned with the direction in which the of the fibres 16 are elongated. The cut lines 18 are represented in FIG. 2 by dashed lines. Although the cut lines 18 are shown in FIG. 2 being located relatively near to each other, being spaced by only about 250 μm, it will be appreciated that neighbouring cut lines 18 can be spaced apart to different extents to produce a strip 14 having a desired width. In one embodiment the strips 14 have a width of between 50 μm to 5 mm. In another embodiment the strips 14 have a width of between 1 mm to 3 mm. In yet another embodiment the strips 14 have a width of about 2 mm. In this way each of the strips 14 will comprise at least some of the fibres 16 running continuously along the entire length of the strip 14. In some embodiments a selection of the width of the strip 14 and a selection of the alignment of the cut lines 18 is made so that at least 50% of the fibres 16 in the strip 14 will run continuously along the entire length of the strip 14. In another embodiment at least 80% of the fibres 16 in the strip 14 will run continuously along the entire length thereof. In still a further embodiment at least 90% of the fibres 16 in the strip 14 will run continuously along the entire length thereof.

It will be appreciated that in some embodiments the strips 14 can be cut so as to comprise a single fibre 16.

Figure 3:
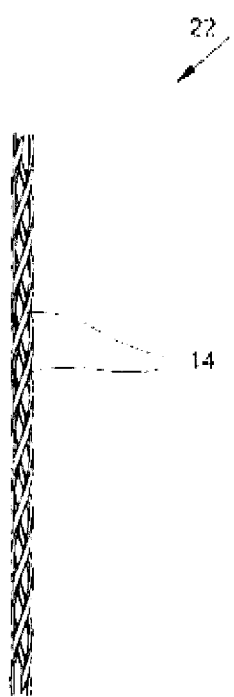
FIG. 3 shows a collagen construct in the form of a collagen rope made from the elongated strips cut from the collagen scaffold of FIG. 1.

One or more of the strips 14 are subsequently amassed in a manner to form the collagen construct. Prior to such amassing, the strips 14 optionally may be rolled along their length, i.e. parallel to the alignment of the fibres 16, to form columnar or tubular shapes. Alternatively the strips 14 can be twisted or spun to form an elongated thread. In one embodiment shown in FIG. 3, the strips 14 are braided together to form a collagen construct in the form of a collagen rope 22. The braid can be a relatively tight braid to form the collagen rope 22 having a relatively rigid columnar structure. Alternatively, the braid can be a relatively loose braid with less structural rigidity and thus provided more flexibility. The selection of a tight braid or loose braid will depend on the target location in a patient's body requiring replacement of a tendon or ligament and the requisite mechanical properties that need to be exhibited. In some embodiments the loose braid or plait pattern is preferred as it reduces shear forces within the strips 14 caused by abutting pressure from adjacent strips 14 during flexing or tensioning of the collagen rope 22.

In some embodiments the collagen rope 22 can comprise three or more strips 14 that are braided together. In other embodiments the collagen rope 22 can comprise three or more strips 14 that are plaited together. If it is desired to have the resultant collagen construct that is even thicker than the collagen rope 22, then multiple collagen ropes 22 can be braided or plaited together to form a collagen cable.

In some embodiments, the collagen rope 22 has a length of between 0.5-50 cm, typically between about 1-25 cm, and in some embodiments between about 2-20 cm. In some embodiments the collagen rope 22 can have a cross-sectional area of between about 0.002-6 mm$^2$, typically between about 0.6-2 mm$^2$. In some embodiments the collagen cable can have a cross-sectional area of between about 1-18 mm$^2$. In one embodiment the collagen construct has a diameter of 10 mm and a cross-sectional area of about 75-80 mm$^2$. In some embodiments, the collagen rope 22 or collagen cable is able to withstand a maximum tensile load of 650 N without breaking or suffering any permanent deformation or damage. The term "maximum tensile load" as used herein refers to the maximum tensile load that the collagen rope can bear. On a Load v Extension curve this is represented by the peak load on the curve.

The collagen rope 22 can optionally include, e.g., be coated, impregnated and/or amalgamated with a gel or other material. The coating may be arranged to promote fibroblasts, and/or comprise one or more of an anti-inflammatory agent, an antibiotic or other therapeutic agent.

The collagen rope 22 is biocompatible and may be absorbed, resorbed and/or biodegradeable over time.

The collagen rope 22 can be configured to have similar or greater tensile strength, stiffness and dynamic flexibility corresponding to natural tendons or ligaments, such as a natural anterior cruciate ligament (ACL). Embodiments of the present disclosure are particularly suitable for augmenting, repairing or replacing tendons and ligament, particularly ACL that may have ruptured. In such cases the collagen rope 22 is configured, sized and shaped to define an ACL. Optionally, the collagen rope 22 can be implanted in a patient using one or more of a suture, suture anchor, bone anchor, bone tunnel and the like. Typically, the collagen rope 22 will be implanted at the site of the repair and secured in place by any conventional means known to those skilled in the art, e.g. suturing, suture anchors, bone fixation devices and bone or biodegradable polymer screws.

The collagen rope 22 can be provided in a medical kit for ACL replacement. The medical kit comprises an implantable collagen construct as described above and a sterile package hermetically enclosing the collagen construct therein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An anterior cruciate ligament (ACL) prosthesis:
a plurality of elongate strips that have been cut from a collagen membrane comprising greater than 80% type I collagen and numerous collagen fibres,
wherein each elongate strip comprises a plurality of collagen fibres,
wherein a majority of the collagen fibres, are aligned parallel to each other in a common direction,
wherein each collagen fibre has a length,
wherein each elongate strip has a length of 2 cm to 20 cm, a thickness of 50 μm to 400 μm, and a width of 50 μm to 5 mm,
wherein the lengths of a majority of the plurality of collagen fibres are aligned along the length of the respective elongate strips;
wherein the plurality of elongate strips are braided, plaited, woven, twisted or wound together to produce the ACL prosthesis,
wherein the ACL prosthesis has a diameter of less than or equal to 10 mm, a cross-sectional area of about 75-80 mm², and is able to withstand a tensile load of 650 N without breaking or suffering any permanent deformation or damage.

2. The ACL prosthesis of claim 1, wherein at least one of the collagen fibres in each elongate strip extends continuously along the entire length of its respective elongate strip.

3. The ACL prosthesis of claim 1, wherein at least 50% of the collagen fibres in each elongate strip extend continuously along the entire length of each respective elongate strip.

4. The ACL prosthesis of claim 3, wherein at least 80% of the collagen fibres in each elongate strip extend continuously along the entire length of each respective elongate strip.

5. The ACL prosthesis of claim 1, wherein each elongate strip has a thickness of 100 μm to 200 μm.

6. The collagen construct of claim 1, wherein each elongate strip has a width of 1 mm to 3 mm.

7. The ACL prosthesis of claim 1, comprising a plurality of braided, plaited, woven, twisted or wound elongate strips that themselves are braided, plaited, woven, twisted or wound together to form the ACL prosthesis.

8. A method for producing an ACL prosthesis of claim 1, comprising the steps of:
a) forming a collagen membrane comprising numerous collagen fibres, wherein a majority of the fibres are aligned parallel to each other in a common direction;
b) cutting the membrane along cut lines such that a majority of the collagen fibres are aligned parallel to each other in a common direction, thereby to separate elongate strips from the membrane; and
c) braiding, plaiting, weaving, twisting or winding together the elongate strips to form the ACL prosthesis.

9. The method of claim 8, further comprising the step of treating the membrane with acetone and subsequently drying the membrane, thereby to fix the collagen fibres in their aligned orientation.

10. The method of claim 8, further comprising cutting the membrane in a manner so that each strip has a width sufficient that at least one of the collagen fibres extends continuously along the entire length of its respective strip.

11. The method of claim 8, wherein step c) further comprises joining sufficient strips together to produce a collagen rope of a sufficient size for use as an anterior cruciate ligament prosthesis.

12. A medical kit for anterior cruciate ligament (ACL) replacement comprising (a) the ACL prosthesis of claim 1; and (b) a sterile package enclosing the ACL prosthesis.

13. A method of repairing anterior cruciate ligament (ACL) tears, partial or complete, comprising:
providing the ACL prosthesis of claim 1;
implanting the ACL prosthesis to augment, repair or replace the ACL; and
securing the ACL prostheses in place.

* * * * *

UNITED STATES PATENT AND TRADEMARK OFFICE
CERTIFICATE OF CORRECTION

PATENT NO. : 10,524,895 B2  
APPLICATION NO. : 15/514804  
DATED : January 7, 2020  
INVENTOR(S) : Zheng Page 1 of 1

It is certified that error appears in the above-identified patent and that said Letters Patent is hereby corrected as shown below:

In the Claims

At Column 9, in Line 5, "An anterior cruciate ligament (ACL) prothesis:" should be --An anterior cruciate ligament (ACL) prothesis comprising:--.

At Column 10, in Line 38, "securing the ACL protheses in place." should be --securing the ACL prothesis in place.--.

Signed and Sealed this  
Nineteenth Day of May, 2020

Andrei Iancu  
*Director of the United States Patent and Trademark Office*